United States Patent [19]

Cronkrite

[11] 4,299,223
[45] Nov. 10, 1981

[54] TAPE TAB FASTENER FOR DISPOSABLE DIAPER

[75] Inventor: William E. Cronkrite, Westmont, Ill.

[73] Assignee: 3 Sigma Inc., Covington, Ohio

[21] Appl. No.: 151,787

[22] Filed: May 21, 1980

[51] Int. Cl.³ .................... A61F 13/16; A41B 13/02; A44B 18/00; A41F 1/00
[52] U.S. Cl. .......................... 128/287; 128/DIG. 30; 156/227; 156/299; 156/300; 156/302; 428/40; 428/130; 428/195; 428/201; 24/304
[58] Field of Search .................... 128/287, DIG. 30; 428/40, 130, 194, 195, 201; 156/227, 299, 300, 302

[56] References Cited

U.S. PATENT DOCUMENTS 4,237,887 12/1980 Gobran .................. 428/40

*Primary Examiner*—Marion McCamish
*Attorney, Agent, or Firm*—Robert E. Wagner; Ralph R. Rath

[57] ABSTRACT

A diaper tape tab includes a backing web having a first pattern of adhesive on one surface thereof and a release coating covering a portion of the other surface with a tape segment secured to the release coating and the exposed portion of the other surface by a second pattern of adhesive. The two adhesive patterns are spaced parallel strips of adhesive that are spaced from each other by a dimension which is less than the width of the strips and the outside strips are spaced inwardly of the lateral edges so that the adhesive is not exposed during storage.

15 Claims, 7 Drawing Figures

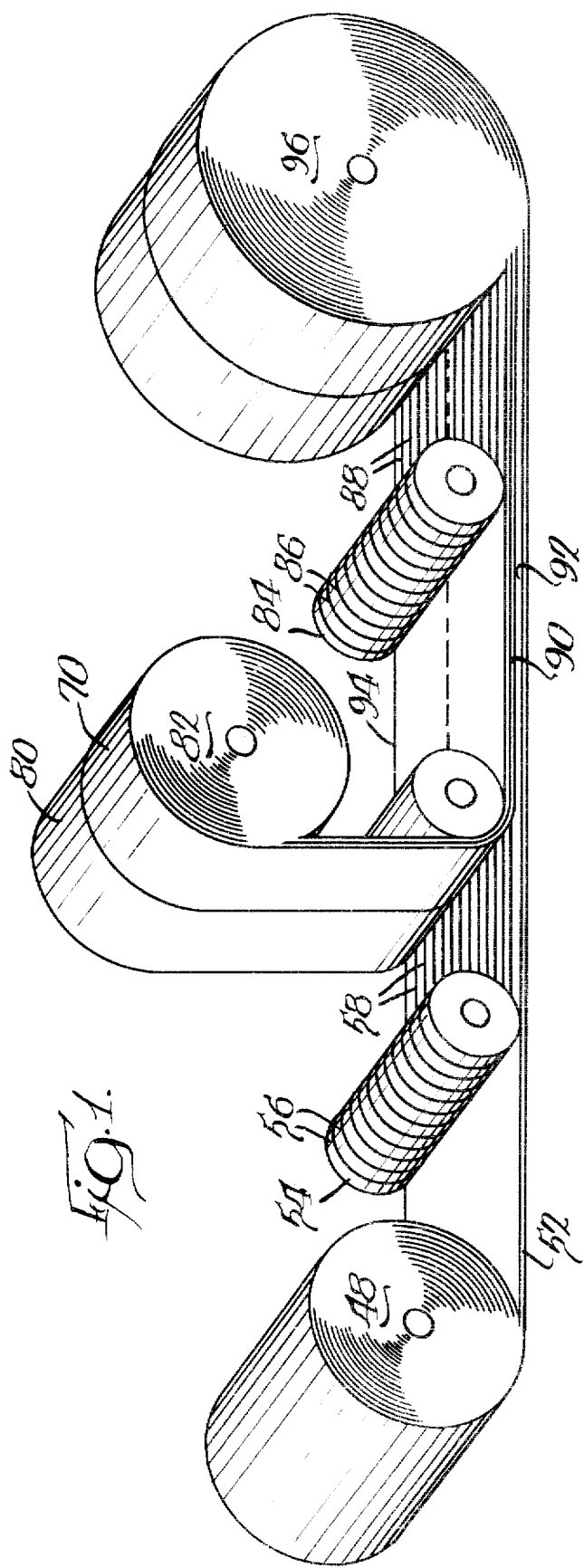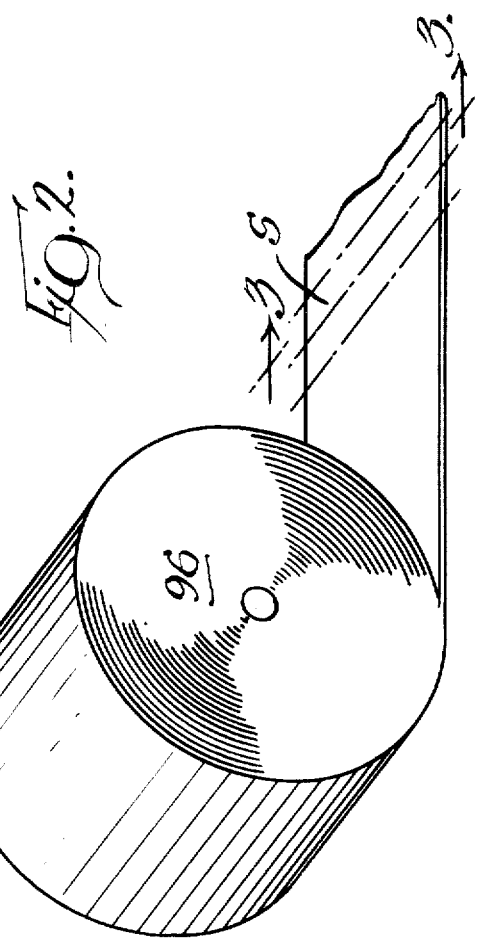

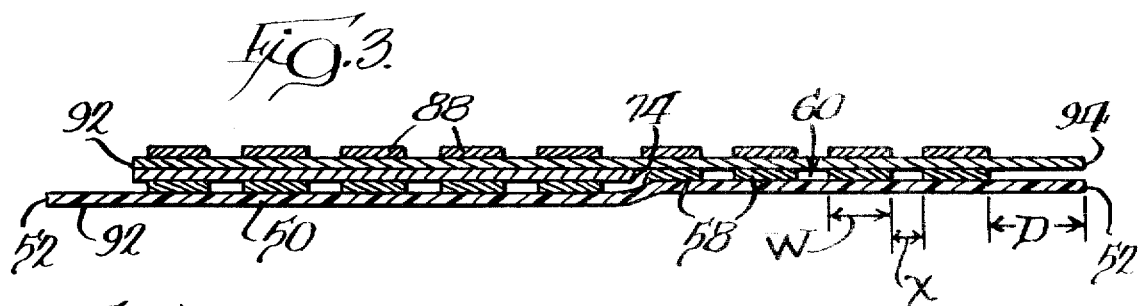
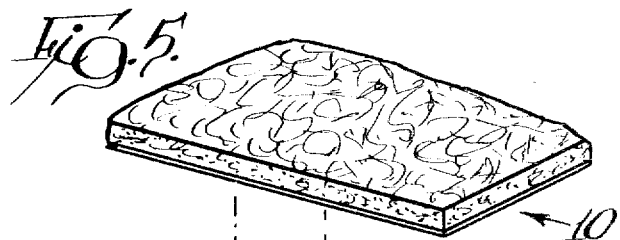
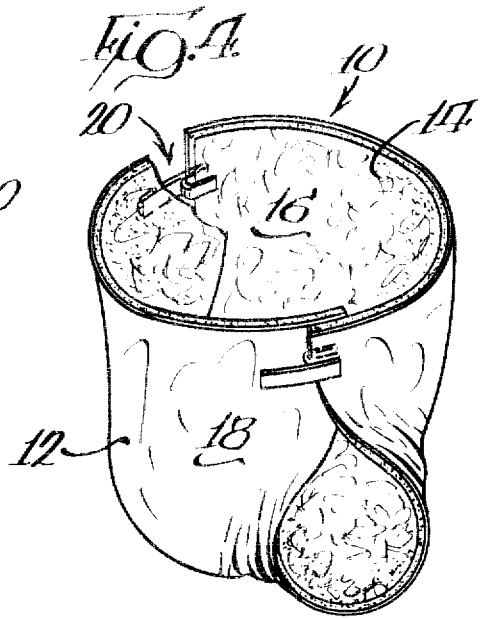
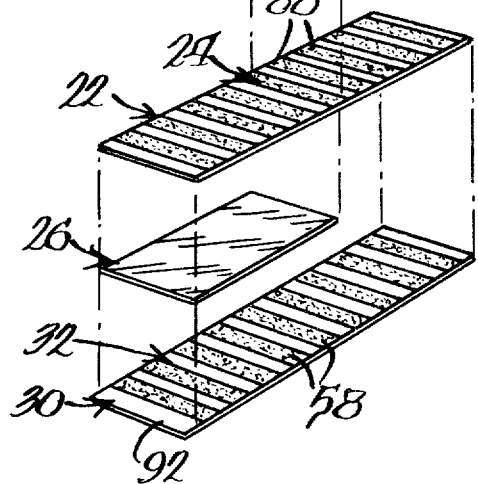
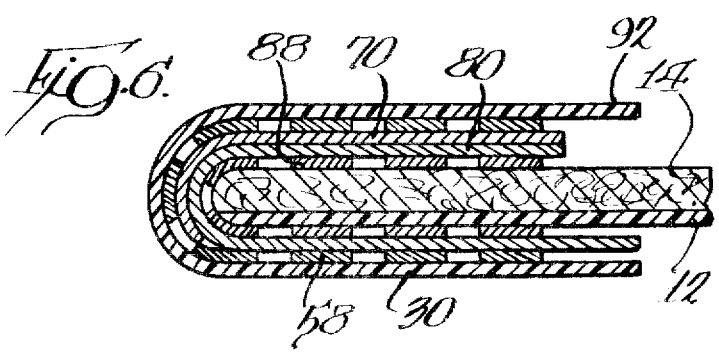
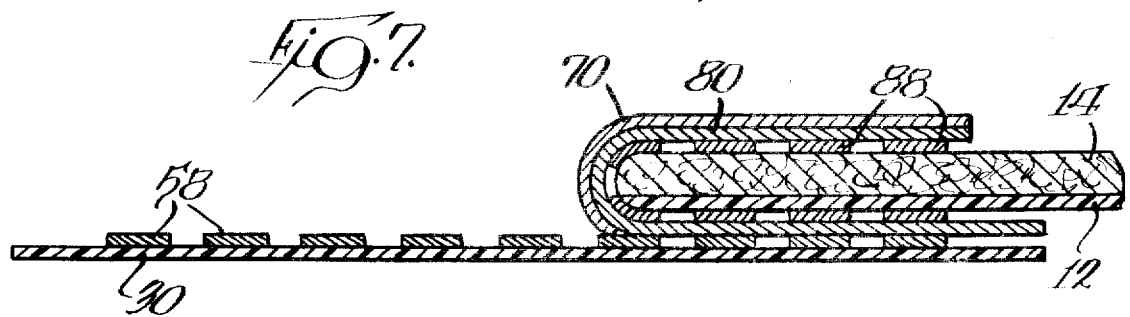

TAPE TAB FASTENER FOR DISPOSABLE DIAPER

DESCRIPTION

Technical Field

The present invention relates generally to disposable diapers and more particularly to diapers of the type having adhesive permanently attached fastener systems associated therewith so that the diapers can be placed on an infant without the use of extraneous fasteners.

Background Prior Art

Disposable diapers have been in use for some time and provide substantial advantages and convenience over reusable diapers that were conventional for many years. Disposable diapers that have recently been developed and are presently marketed have incorporated significant improvements which make these diapers more functional and desirable than the type that are intended to be laundered and reused.

With new fabrics that have been developed, the disposable diaper structure usually consists of a fluid-porus fiberous woven or non-woven substrate which defines an absorbent core. A porus, fiberous sheet is applied to one surface, the intended inner surface adapted to be disposed adjacent the body of the infant and a moisture-impervious backing sheet which defines the outer surface of the diaper and generally is made from a plastic film such as polyethylene film or the like. With the increased acceptance of disposable diapers by the purchasing public, considerable emphasis has been directed towards the development of an acceptable type of tab fastener which can be permanently attached to the diaper during the construction thereof and can be used subsequently without the need for any additional fastening elements or special tools. The typical type of fastener tabs that have been utilized in conjunction with disposable diapers generally consist of some type of tab structure which has an adhesive coating on one surface thereof, a portion of which is permanently attached to a marginal edge of the diaper and the remainder of which has a removable cover strip or release means applied to the adhesive surface thereof which can be subsequently removed when the diaper is about to be used and attached to an over-lapping marginal edge of the diaper to hold the diaper on the infant.

One of the problems with this type of tab construction is the fact that the tab portion with the release coating thereon extends beyond the marginal edge of the diaper which complicates the automation of packaging of the product and displaying the product.

Thus, other types of tab fasteners have been proposed which are folded over the marginal edge of the disposable diaper when initially installed and a portion thereof is subsequently separated to extend beyond the marginal edge of the diaper and acts as the fastener when the diaper is placed in use. Examples of this type of fastener means are disclosed in U.S. Pat. No. 3,875,621; 3,999,546; and 4,020,842.

In recent years attempts have been made to enhance the appearance of the plastic outer sheet by embossing the outer surface of the sheet to emulate a cloth appearance. In so doing, difficulties have been encountered in maintaining a permanent bond between the tab inner surfaces and the outer surface of the diaper because of the irregular contour of the diaper surface. This is particularly true when using hot melt adhesives which have a tendency to stiffen the material.

Tab stock is usually formed in a separate operation, many times in a separate plant, and is stored and transported in large rolls. The tab stock is formed by feeding an endless supply of a backing sheet and applying an adhesive across one surface thereof, which is ultimately attached to the diaper, and covering the adhesive with a release member. Another web of material also has an adhesive applied to one surface thereof and is adhered to the other surface of the backing sheet with a release member interposed between a portion of the backing sheet and web. The tab stock is then stored in a roll until it is ultimately severed into little strips. The exposed release coating is removed and the exposed surface of the backing sheet is attached to the diaper along a marginal edge.

In forming the tab stock as described above, particularly when using hot melt adhesive, the adhesive tends to flow to the edges of the backing web or sheet as well as the web of tab material and remains exposed during storage and shipment prior to actual application to the diaper. The exposed edges of adhesive on the tab stock have a tendency to accumulate dust, lint and dirt which not only detracts from the appearance but also creates a sanitation problem.

Summary of the Invention

According to the present invention, a unique tab construction has been developed which can be attached to the marginal edge of a product, particularly a disposable diaper, which includes a backing sheet defining an outside surface and a facing sheet defining a diaper inside surface with a fiberous core between the sheets.

According to the present invention, a supply of web stock for use in forming tabs that are adapted to be attached to a marginal edge of a disposable diaper, includes an endless backing web having opposite lateral edges with a first adhesive coating on one surface thereof and a removable release web on said surface with a tab web having a second adhesive coating on one surface and adhered to an opposite surface of the backing web with a second release web between a portion of the tab web and the backing web.

The first adhesive coating between the backing web and the removable release web consists of a plurality of parallel spaced strips of adhesive that extend parallel to lateral edges of the backing web and the respective strips that are adjacent the respective lateral edges are spaced inwardly by a predetermined dimension so that the opposite edges of the tape stock are devoid of any adhesive. The adhesive coating between the tab web, the second release web and the remainder of the backing web has a pattern which is substantially identical to the pattern of the first adhesive coating and in the preferred form, the predetermined dimension between the edge and the first adhesive strip is greater than the width of the respective adhesive strips, which are preferably equal in width, while the spacing between adjacent strips is less than the width of each of the strips.

With the above supply of tab stock, the tab stock can be rolled on a roll and stored for any given period of time without any exposed edges of adhesive which could pick up dirt, lint and other contamination.

When tabs are to be produced for attachment to a disposable diaper, it is only necessary to sever a tab of predetermined width from the endless supply of stock, remove the release coating from the first layer of strips of adhesive on the backing surface and then permanently attach the backing surface to opposite surfaces of the disposable diaper by folding the tab intermediate opposite ends.

If the tab stock is stored in rolls, the removable release coating can be eliminated and the first adhesive coating can engage the exposed surface of the tab web during storage on the roll.

The attached tab consists of a backing web that has opposite edges and opposite ends with an inner face that has an adhesive securing area permanently attached to the marginal edge of a diaper and in contiguous engagement with the inside surface or backing sheet along one portion thereof and the outside surface or facing sheet.

The tab also has a second release coating or web between the backing web and the adhesive pattern of the tab web which extends from one end of the backing web and terminates intermediate opposite ends. An elongated tab segment that is substantially coterminous with the backing web has marginal edges and marginal ends which are in juxtaposed relation to the marginal edges and marginal ends of the backing web, with one exception, with a second adhesive means for securing the tape segment to the release coating as well as the remaining exposed portion of the backing web.

Thus, the adhesive means for attaching the backing web to the exposed surfaces of the disposable diaper has a pattern that consists of a plurality of longintudinally spaced narrow lines of adhesive that extend generally parallel to opposite ends of the backing web and are spaced from each other. The spacing between the respective strips or lines of adhesive allows for substantial flexibility of the tape tab along lines transversely of the length of the tab and a limited amount of flexibility with respect to lines along the longintudinal dimension of the web to allow the web to conform to irregularities in the surface of the disposable diaper when attached thereto.

The adhesive means for attaching the tape segment to the backing web also has a pattern which corresponds substantially to the pattern of the adhesive means between the backing web and the disposable diaper. Again, the adhesive pattern consists of longintudinally spaced parallel lines of adhesive that extend generally parallel to opposite ends of the tape segment.

Brief Description of Several Views of Drawings

FIG. 1 of the drawings schematically illustrates a method of producing a supply of tab stock material;

FIG. 2 is a perspective view of a supply of tab stock, illustrating how individual tabs are severed;

FIG. 3 is a cross-sectional view as viewed along line 3—3 of FIG. 2;

FIG. 4 of the drawings discloses a disposable diaper having a tab constructed in accordance with the present invention associated therewith;

FIG. 5 is an exploded perspective view of the components of the tab;

FIG. 6 is a cross-sectional view of the tab attached to the diaper prior to the diaper being used; and, FIG. 7 is a cross-sectional view showing the tab in its final position for attaching marginal edges of the diaper.

Detailed Description

While this invention is susceptible of embodiment in many different forms, there is shown in the drawing and will herein be described in detail a preferred embodiment of the invention with the understanding that the present disclosure to be considered as an exemplification of the principle of the invention and is not intended to limit the invention to the embodiment illustrated.

FIG. 4 of the drawings discloses a diaper, generally designated by reference numeral 10 having an absorbent pad (not shown) that is covered on one surface thereof by a moisture-impervious outer material, such as a polyethylene plastic 12 and an inner backing sheet or liquid pervious member 14. The marginal edges of members 12 and 14 are permanently attached to each other to entrap the moisture absorbent pad (not shown) in the centrally disposed portion thereof. The backing sheet defines an inside surface 16 which is adapted to be directed towards the body of an infant and the liquid impervious outer sheet has an outside surface 18. As indicated above, it is many times desirable to have the outer surface embossed with some type of pattern to enhance the appearance of the product for display purposes. Usually the embossed pattern is placed on the backing sheet before the backing sheet is separated from the supply and cut into the final pattern. Thus, when a randomly placed pattern is embossed on the backing sheet it results in an irregular contour on the surface of the backing sheet where the tab must be attached thereto.

According to the present invention, the tab 20 is constructed in such a fashion so as to be extremely flexible to readily adhere to or conform to irregularities of the surface to which it becomes attached. As illustrated in FIG. 5, tab 20 consists of a first backing web 22 which has adhesive means 24 on one surface thereof adapted to be permanently attached to the marginal edge of diaper 10. A release coating web or means 26 is located on the surface of backing web 22 which is opposite the surface having adhesive means 24 thereon and release web 26 is preferably approximately one-half the length of elongated backing web 22, for a purpose that will be described later. The third element of the tab 20 consists of a tab segment or web 30 which is preferably formed from a material, that has good strength characteristics. Tab tape segment 30 again has adhesive means 32 on one surface thereof for attachment to the exposed surface of release web 26 as well as the remaining exposed surfaces of backing web 22.

According to the primary aspect of the present invention, tab 20 is severed from a continuous supply of tab stock material that is formed in a unique fashion to have superior characteristics, particularly with respect to the adhesive surfaces that form the attaching means for attaching the tab to the diaper and also for the adhesive means that is utilized for inte connecting opposite ends of a marginal edge of the di per when applied on an infant. The machinery utilized for assembling the tab stock is well-known and commercially available and need not be shown or described.

With reference to FIG. 1 of the drawings, an endless supply of a tape web 50 is supported on a supply roll 48 and is moved along a path P with marginal edges 52 on opposite edges of the path. An adhesive coating roller 54 is located along the path for the tape web 50 and has a plurality of lines of adhesive supplying means 56 formed thereon. The adhesive supplied to the web 50 is preferably a hot melt adhesive and the respective strips of adhesive 56 produce a plurality of transversely spaced parallel strips of adhesive 58 on the surface of the tape web 50.

In FIG. 3 of the drawings, the particular pattern of strips of adhesive 58 is illustrated in detail and it will be noted that the respective strips of adhesive 58 extend generally parallel to each other and opposite edges 52 and have spacings 60 of predetermined width between adjacent strips. Also, the respective strips 58 which are located adjacent opposite lateral edges 52 are spaced inwardly from the edges 52 by a predetermined dimension D. The width of strips W has a specific relation to the width X of spacings 60 and with respect to the predetermined dimension D.

According to the invention, the width of the spacing between the edge 52 and the first strip 58 is greater than the width W of the respective strips, which are equal to each other and the width of each strip is greater than the width of the spacing between adjacent strips. By way of example and not of limitation, the width W of each strip or bead is about 10.0 mm (0.040") to about 12.7 mm (0.050") while the spacing X between adjacent beads of adhesive 58 may be in the range of about 5.0 mm (0.020") to about 7.6 mm (0.030"). Also, the predetermined dimension D between lateral edge 52 of tape web 50 and the adjacent edge of the first strip is approximately 15.25 mm (0.060"). The significance of this feature will be described in more detail later.

A release coating 70 is applied to approximately one-half of the adhesive surface of tape web 50. In the illustrated embodiment, the release web is initially applied to a surface of a liner web 80. Liner web 80 and release coating web 70 are wound onto an endless roll 82.

The roll 82 is aligned with web 50 and is moved across an idler roll 84 which forces the exposed surfaces of release or roller coating 70 and web 80 into engagement with the adhesive surface of web 50.

A second adhesive applying means or roller 86 applies a pattern of strips of adhesive 88 which correspond substantially to the pattern of strips 58, as explained above. The aligned edges 80 of liner web 80 and release web 70 are spaced inwardly of an adjacent edge 52 of tape web 50 so that there is an exposed gripping portion 92, as illustrated in FIG. 3. The opposite lateral edge 94 of web 80 is again aligned with the opposite lateral edge 52, as shown in FIG. 3.

The tab material is preferably then formed on a roll 96 which has lines of adhesive 88 secured to the exposed surface of backing web 50. If desired, a further release web (not shown) may be applied to adhesive strips 88. However, it has been found that such additional release web is unnecessary.

From an inspection of FIG. 3 it will be noted that the entire adhesive pattern or strips 58 and 88 are spaced inwardly from the lateral edges of the backing member and release web so that there is no exposed adhesive along either of the lateral edges of the roll of material 96 when it is in a condition for transportation and storage. Thus, during the substantial period of time during which the roll 96 may be stored in a warehouse, no exposed adhesive edges are visible on opposite edges of the roll 96 resulting in a more functional supply of tape having greater shelf life since there is no exposed adhesive which will attract dust, lint or dirt.

When a tab is needed for attachment to a disposable diaper, strips S (FIG. 2) of desired width are severed from roll 96 along lines 99. For example, a tab S could have a width of about one inch.

In each strip S which defines a tape tab 20, adhesive means 24 is defined by strips 88 applied in a predetermined pattern to increase the flexibility of the overall tape tab 20. More specifically, adhesive means 24 consists of a plurality of spaced parallel strips 88 which extend parallel to opposite ends 42 of backing web or liner 22.

The second pattern of adhesive 32 which is identical to the pattern of adhesive means 24, is defined by strips of adhesive 58 on the inner surface of the tape segment 30. In this respect, the portion 92 of the tab web which defines tape segment 30 extends beyond the adjacent release web so that an end portion 92 extends beyond the adjacent end 42 of backing web 22 to define a finger grip for subsequent release, as will be described later.

As illustrated in FIG. 6, the tab 20 is attached to diaper 10 by folding it at the approximate midpoint thereof and the adhesive 24 is used to attach the backing web 22 to the inner surface 16 as well as the outer surface 18 of the diaper 10. As illustrated in FIG. 6, the portion of tab 20 which has release coating 26 thereon is attached to inner surface 16 of the diaper while the portion which has backing web 22 and tape segment 30 permanently attached to each other is attached to surface 18.

Two such tabs are located in opposed relation to each other along opposed marginal edge of the diaper adjacent one end thereof and are generally equally spaced from the adjacent end of the diaper. When the diaper is to be placed on an infant, the finger gripping portions 92 are grasped and the tape segment 30 is separated from the release coating so that the tape segment is generally flat and the portion thereof extends beyond the lateral edge of the diaper to which the remainder of the tab is attached. The diaper is then wrapped around the legs of the infant and the exposed tab segment is attached to the opposite end of the adjacent marginal edge of the diaper so that the diaper is properly positioned on the infant.

As can be appreciated from the above description, the particular adhesive pattern and the spacing between the strips of adhesive increases the flexibility of the entire tab and allows it to more readily conform to irregular contours on the surface of the diaper. Also, the particular adhesive pattern, particularly the spacing of the separate lines of adhesive reduces the amount of adhesive necessary for manufacturing the tab and attaching the tab to the diaper. In addition, if desired, the width of the release layer or web 26 may be reduced by an amount which is equal to the predetermined dimension D between the marginal edge 52 of backing web 22 and the first strip of adhesive 58.

Since each of the strips of adhesive has a width which is substantially less than the width of the tape tab, between the marginal edges thereof, and in fact is many times less than the width of tab 20, the narrow bands of adhesive will also increase the flexibility of the tab and will reduce the amount of adhesive needed and the surface area covered which reduces the overall stiffening of the tab resulting from the adhesive.

The material used for the backing web and the tape segment can vary but it is preferable to use a plastic material, such as polypropelene and the tape segment may be a latex saturated paper. Also, in some instances it may be desirable to eliminate the release web 62 entirely and adhere the adhesive strips directly to the exposed surface of tape segment 80 while the tab stock is stored in roll form.

Of course, the number of strips of adhesive 58 or 86 can be varied and will also be dependent upon the length of tab 20, and the number of strips shown in the drawings, is for purposes of illustration and not intended to be limited to such number.

I claim:

1. A supply of tab stock for use in forming tabs adapted to be attached to a marginal edge of a diaper, comprising a backing web having first adhesive coating on one surface thereof between lateral edges and a removable release web on said surface, and a tab web having a second adhesive coating on one surface thereof and adhered to an opposite surface of said backing web with a second release web between a portion of said tab web and said backing web, the improvement of said first adhesive coating comprising a plurality of parallel strips of adhesive extending parallel to said lateral edges with each of said strips being substantially equal in width and with the respective strips adjacent said lateral edges being spaced from the lateral edges by a predetermined dimension so that opposite edges of said tab stock are devoid of adhesive.

2. A supply of tab stock as defined in claim 1, in which said predetermined dimensions are greater than the width of said strips of adhesive.

3. A supply of tab stock as defined in claim 2, in which the spacing between adjacent strips is less than the width of said strips.

4. A supply of tab stock as defined in claim 1, 2 or 3 in which said second adhesive coating has a pattern substantially identical to said first adhesive coating.

5. A supply of tab stock as defined in claim 1, further including a removable release web covering said first adhesive coating.

6. A supply of tab stock as defined in claim 1, in which said second release web has a width approximately one-half the width of said backing edge and has one edge aligned with one of said lateral edges and in which an adjacent edge of said tab web extends beyond said one of said lateral edges to define a finger gripping portion free of any adhesive.

7. A method of forming a tab for use with a disposable diaper comprising the steps of feeding a backing web of material along a path, applying a plurality of strips of adhesive to one surface of said backing web parallel to said path with the respective strips being spaced from each other transversely of said path and with the respective strips along opposite edges of said backing web being spaced inwardly of said edges, feeding a tab web toward said path and applying a plurality of second strips of adhesive to a surface of said tab web parallel to said path and transversely spaced from each other with the respective strips adjacent opposite lateral edges, feeding a release web of less width than said backing web between said surface of said tab web and an exposed adjacent surface of said backing web and adhering said second strips of adhesive to said release web and an exposed portion of adjacent surface of said backing web.

8. A method as defined in claim 6, including the further step of collecting said backing web on a roll with said strips of adhesive on said backing web adhered directly to an exposed surface of said tape web.

9. A method as defined in claim 6, including the further step of applying a removable release coating to the exposed surface of said adhesive on said backing web and collecting said tab on a roll for storage.

10. A disposal diaper having a facing sheet defining a diaper inside surface adapted to be directed toward an infant and a moisture-impervious backing sheet having an outside surface with a peripheral edge, and a pair of tabs secured to said edge, each of said tabs including a backing web having opposite edges and opposite ends with first adhesive means permanently attached to said inside and outside surface along said marginal edge and an outside face with release means on said outside face along said inside surface, a tape segment overlying said outside face and said release means with said tape segment having opposite edges and opposite ends and second adhesive means securing said tape segment to said release means and exposed portion of said outside face, the improvement of said first adhesive means including a plurality of spaced lines of adhesive extending generally parallel to said opposite ends of said backing web and adhered to said outside surface to provide flexibility to said backing web to conform to irregularities on said outside surface, each of said lines of adhesive having a width which is many times less than the width of said web to increase the flexibility of said tab.

11. A disposable diaper as defined in claim 10, in which said second adhesive means defines a pattern on said tape segment corresponding substantially to the pattern of said first adhesive means on said backing web.

12. A disposable diaper as defined in claim 11, in which said backing web and said tape segment are substantially coterminous with said tape segment having an integral extension extending beyond said release means devoid of said second adhesive to define a release finger gripping portion.

13. An adhesive tab means for a disposable diaper having a marginal edge, an inside surface for direction toward an infant and an outside surface, comprising an elongated backing web having opposite edges and opposite ends with an inner face and an outer face, said inner face having first adhesive adapted to be permanently attached to the diaper surfaces along said marginal edge, release means on a portion of said outer face of said backing web extending from one end and terminating intermediate opposite ends, an elongated tape segment substantially coterminous with said backing web and having marginal edges and opposite ends, and second adhesive means securing said tape segment to said release means and the exposed portion of said outer face of said backing web, the improvement of each said adhesive means comprising a plurality of longitudinally spaced strips of adhesive extending generally parallel to said opposite ends the width of each strip and the spacing of each adjacent pair of strips being many times less than the width of said tab means to provide flexibility for attaching the tab means to the diaper.

14. A tab means as defined in claim 13, in which said adhesive strip has a width greater than the spacing between adjacent strips of adhesive.

15. A tab means as defined in claim 14, in which said tape segment has a finger grip extension extending beyond said one end of said backing web and being free of said backing web to be utilized to separate said tape segment from said backing web along said release means.

* * * * *